(12) United States Patent
Su et al.

(10) Patent No.: US 10,314,470 B2
(45) Date of Patent: Jun. 11, 2019

(54) BODY CAVITY ILLUMINATION APPARATUS

(71) Applicant: Ribcure Co., Ltd., Taichung (TW)

(72) Inventors: Ying-Chieh Su, Tainan (TW);
Chun-Sung Liu, Taichung (TW)

(73) Assignee: Ribcure Co. Ltd., Taichung (TW)

( * ) Notice: Subject to any disclaimer, the term of this patent is extended or adjusted under 35 U.S.C. 154(b) by 234 days.

(21) Appl. No.: 15/616,218

(22) Filed: Jun. 7, 2017

(65) Prior Publication Data
US 2017/0354322 A1   Dec. 14, 2017

Related U.S. Application Data

(60) Provisional application No. 62/350,044, filed on Jun. 14, 2016.

(51) Int. Cl.
*A61B 1/07*  (2006.01)
*A61B 17/34* (2006.01)
*A61B 90/30* (2016.01)

(52) U.S. Cl.
CPC ............ *A61B 1/07* (2013.01); *A61B 17/3417* (2013.01); *A61B 17/3421* (2013.01); *A61B 17/3423* (2013.01); *A61B 90/30* (2016.02); *A61B 2017/3492* (2013.01); *A61B 2090/306* (2016.02)

(58) Field of Classification Search
CPC ................................. A61B 90/30; A61B 1/07
See application file for complete search history.

(56) References Cited

U.S. PATENT DOCUMENTS

| | | | | |
|---|---|---|---|---|
| 2001/0029316 A1* | 10/2001 | Webb | ............ | A61B 5/0071 600/113 |
| 2001/0052930 A1* | 12/2001 | Adair | ............ | A61B 1/00016 348/65 |
| 2004/0064019 A1* | 4/2004 | Chang | ............ | A61B 1/00059 600/180 |
| 2004/0242963 A1* | 12/2004 | Matsumoto | ........ | A61B 1/00096 600/127 |
| 2005/0065453 A1* | 3/2005 | Shabaz | ............ | A61B 10/0266 600/564 |
| 2006/0009682 A1* | 1/2006 | Nagasawa | ............ | A61B 1/07 600/171 |
| 2007/0213745 A1* | 9/2007 | Takemoto | .......... | A61B 17/0469 606/144 |
| 2014/0135584 A1* | 5/2014 | Lee | ........... | A61B 17/02 600/202 |

* cited by examiner

*Primary Examiner* — Christian A Sevilla
(74) *Attorney, Agent, or Firm* — C. G. Mersereau; DeWitt LLP

(57) ABSTRACT

A body cavity illumination apparatus has a position-controlling trocar and an intra-corporeal light element. The position-controlling trocar has a sticker, a positioning device, a trocar tube, and a trocar connector. The sticker has a through hole. The positioning device is deposited on the sticker. The trocar tube is connected to the positioning device, extends through the sticker, and has an inner end and an outer end. The trocar connector is connected to the outer end of the trocar tube. The intra-corporeal light element is detachably mounted in the position-controlling trocar and has a shaft, a shaft connector, a cable connector, and a light cable. The positioning-controlling trocar may provide a holding effect to the intra-corporeal light element without manual holding to keep the position. In use, the intra-corporeal light element may provide an intra-corporeal illumination effect at multi-angles.

12 Claims, 15 Drawing Sheets

BODY CAVITY ILLUMINATION APPARATUS

The present invention is a U.S. Non-Provisional Patent Application of the Provisional application No. 62/350,044, filed on Jun. 14, 2016.

BACKGROUND OF THE INVENTION

1. Field of Invention

The present invention relates to an illumination apparatus for human body cavities such as the peritoneal cavity or pleural cavity, and more particularly to a body cavity illumination apparatus that may hold a light source to provide an intra-corporeal illumination without manual holding to keep the position conveniently, may have a simple structure, may reduce the manufacturing cost, and may operate at multi-angles.

2. Description of the Related Art

Body cavity (peritoneal cavity, pleural cavity, etc.) illumination through a small incision is always an issue in medical surgeries. In a surgical operation, with reference to FIG. 14, an incision 71 is formed on a human body 70 to communicate with an abdominal cavity 72 or a peritoneal cavity of the human body 70, and a wound retractor 73 is deposited on an abdominal wall of the human body 70 to maintain the incision 71. The surgeons traditionally depend on a conventional ceiling light to offer an extracorporeal illumination 80 to enter the abdominal cavity 72 of the human body 70 via the incision 71 to form an interior light beam 81. However, most of the extracorporeal illumination 80 from the conventional ceiling light is blocked by the surgeon's head and is shaded off by the incision 71, and the illuminating range and strength of the interior light beam 81 are much limited to make the organs 74 visible.

With reference to FIG. 15, another way is to provide an intra-corporeal illumination by a conventional video-endoscope system, even in a non-endoscopic surgery. The conventional video-endoscope system has an intra-corporeal light element 90 to provide an intra-corporeal illumination, and the intra-corporeal light element 90 is inserted into the human body 70 and extends in the abdominal cavity 72 to introduce light 91 from an extra-corporeal light source into the abdominal cavity 72. However, the conventional video-endoscope system is expensive, thus the resource of the conventional video-endoscope system in any medical institution is limited. Furthermore, in use, the conventional video-endoscope system needs an assistant to hold it. These factors make practice of the conventional video-endoscope system in an open surgery not so reasonable.

The body cavity illumination apparatus in accordance with the present invention mitigates or obviates the aforementioned problems.

SUMMARY OF THE INVENTION

The primary objective of the present invention is to provide a body cavity illumination apparatus that may hold a light source to provide an intra-corporeal illumination without manual holding to keep the position conveniently, may have a simple structure, may reduce the manufacturing cost, and may operate at multi-angles.

The body cavity illumination apparatus in accordance with the present invention has a position-controlling trocar and an intra-corporeal light element. The position-controlling trocar has a sticker, a positioning device, a trocar tube, and a trocar connector. The sticker has a through hole. The positioning device is deposited on the sticker. The trocar tube is connected to the positioning device, extends through the sticker, and has an inner end and an outer end. The trocar connector is connected to the outer end of the trocar tube. The intra-corporeal light element is detachably mounted in the position-controlling trocar and has a shaft, a shaft connector, a cable connector, and a light cable. The positioning-controlling trocar may provide a holding effect to the intra-corporeal light element without manual holding to keep the position. In use, the intra-corporeal light element may provide an intra-corporeal illumination effect at multi-angles.

Other objectives, advantages and novel features of the invention will become more apparent from the following detailed description when taken in conjunction with the accompanying drawings.

DETAILED DESCRIPTION OF THE INVENTION

Figure 1:
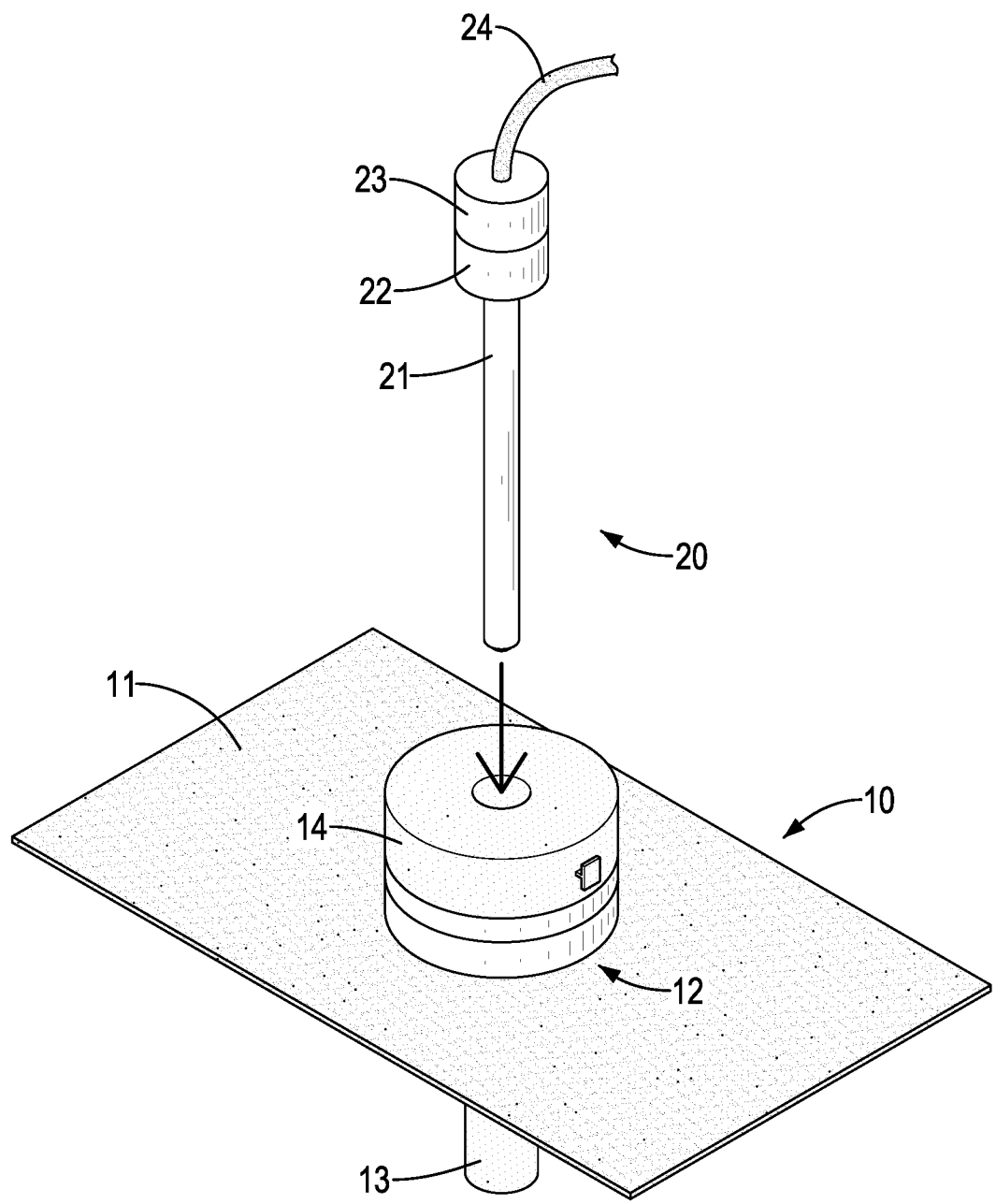
FIG. 1 is an exploded perspective view of a first embodiment of a body cavity illumination apparatus in accordance with the present invention.
Figure 2:
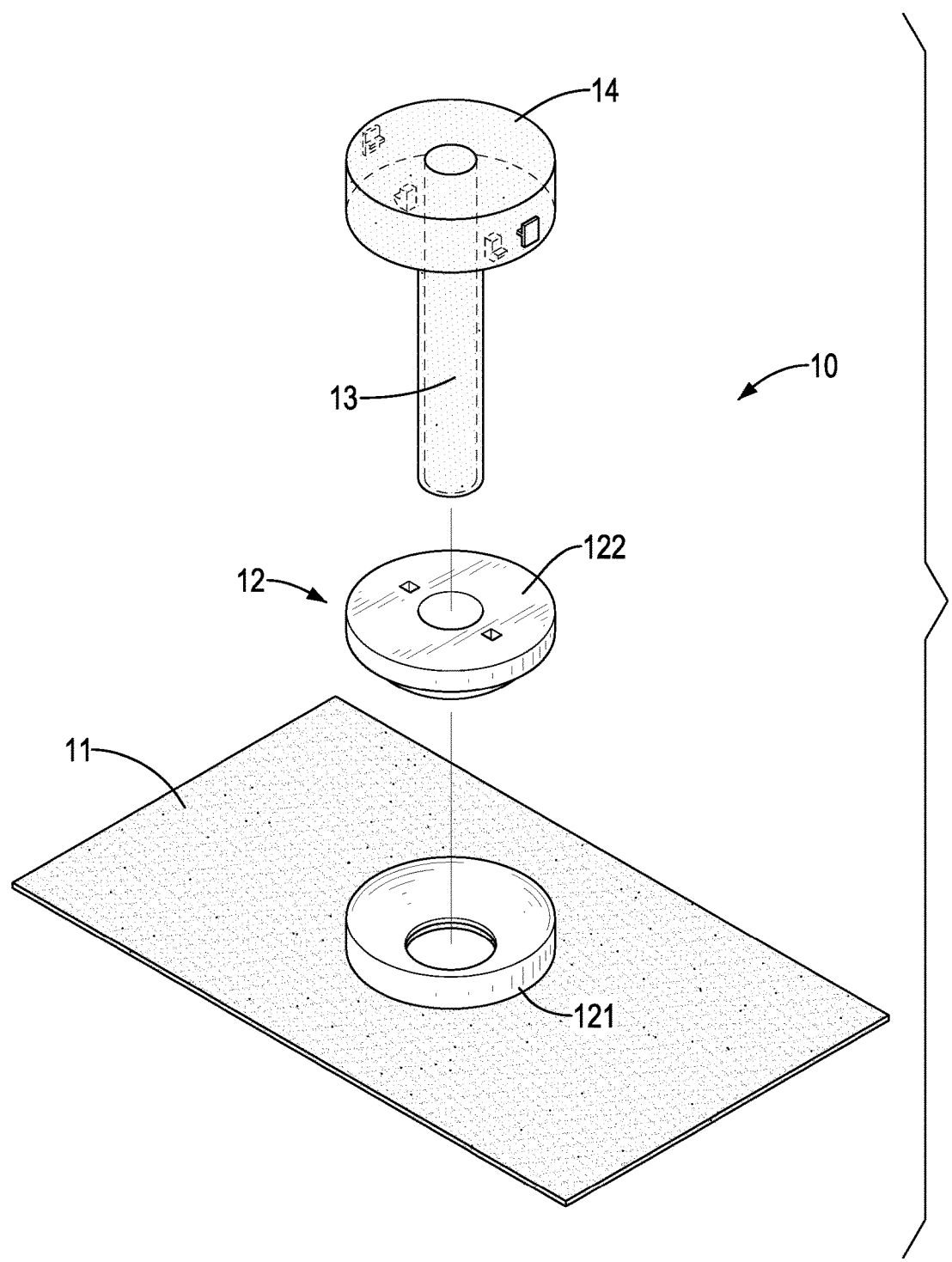
FIG. 2 is an exploded perspective view of a position-controlling trocar of the body cavity illumination apparatus in FIG. 1.

With reference to FIGS. 1 to 4, a first embodiment of a body cavity illumination apparatus in accordance with the present invention is used on a human body 40 to provide an illuminating effect and has a position-controlling trocar 10 and an intra-corporeal light element 20.

The position-controlling trocar 10 is used to deposit on the human body 40 and has a sticker 11, a positioning device 12, a trocar tube 13, and a trocar connector 14. The sticker 11 is deposited on a skin surface of the human body 40 to form a firm position reference for the positioning device 12, and has a bottom side, a top side, and a through hole 111. The bottom side of the sticker 11 abuts the skin surface of the human body 40. The through hole 111 is formed through the top side and the bottom side of the sticker 11. When the sticker 11 is deposited on the skin surface of a patient's body 40, the through hole 111 aligns with a surgical hole 45 that is formed on the human body 40.

The positioning device 12 is deposited on the sticker 11 and has a sticker segment 121 and a moving segment 122. The sticker segment 121 is securely deposited on the top side of the sticker 11. The moving segment 122 is detachably connected to the sticker segment 121 of the positioning device 12. Furthermore, the moving segment 122 is rotatably and/or swingably mounted on the sticker segment 121 of the positioning device 12 by a direct concave-convex contacting manner. For example, the sticker segment 121 may have a concave face formed on a top side of the sticker segment 121, and the moving segment 122 may have a convex face formed on a bottom side of the moving segment 122 and fitted with and corresponding to the concave face of the sticker segment 121. Furthermore, the moving segment 122 further has an assembling hole formed through of the moving segment 122. In addition, the moving segment 122 is securely deposited on the sticker 11 via the sticker segment 121 of the positioning device 12. Further, the positioning device 12 can change in shape, swing, rotate and lock in position according to its design, to change the relative position of the trocar tube 13 to the sticker 11.

The trocar tube 13 which has an inner end, an outer end, and an inner diameter is connected to the positioning device 12, extends through the sticker 11 via the positioning device 12, extends into a body cavity such as an abdominal cavity 42 of the human body 40 via the through hole 111 of the sticker 11. The inner end of the trocar tube 13 extends into the abdominal cavity 42 of the human body 40 via the positioning device 12 and the sticker 11. The trocar connector 14 is connected to the outer end of the trocar tube 13, and selectively engages with the moving segment 122 of the positioning device 12 to hold the trocar connector 14 and the trocar tube 13 with the positioning device 12. Furthermore, the trocar connector 14 is formed with the trocar tube 13 as a single piece.

The intra-corporeal light element 20 is detachably mounted in the position-controlling trocar 10, and extends into the abdominal cavity 42 of the human body 40. The intra-corporeal light element 20 has a shaft 21, a shaft connector 22, a cable connector 23, and a light cable 24. The shaft 21 is inserted into the human body 40 and extends in the abdominal cavity 42 via the trocar connector 14, the positioning device 12, the sticker 11, and the trocar tube 13 to introduce light 30 from an extra-corporeal light source into the abdominal cavity 42. The shaft connector 22 is connected to or coupled to an end of the shaft 21 that extends out of the human body 40. The cable connector 23 is connected to the shaft connector 22 and is opposite the shaft 21. The light cable 24 is connected to the cable connector 23 and is opposite the shaft connector 22, and is connected to a light source, which is an industrial standardized machine. Furthermore, an alternative of the light cable with a light source is a small battery powered LED device, cluster fiber or lens.

Furthermore, the shaft 21 has an outer diameter smaller than the inner diameter of the trocar tube 13 to make the trocar tube 13 contain the shaft 21 of the intra-corporeal light element 20. Additionally, the trocar connector 14 has an inner diameter larger than the outer diameter of the shaft 21 to enable the shaft 21 to pass though the trocar connector 14. After the shaft 21 passes through the trocar connector 14, the shaft connector 22 is connected to or engages with the trocar connector 14, and this may maintain the relative position between the position-controlling trocar 10 and the intra-corporeal light element 20.

Figure 3:
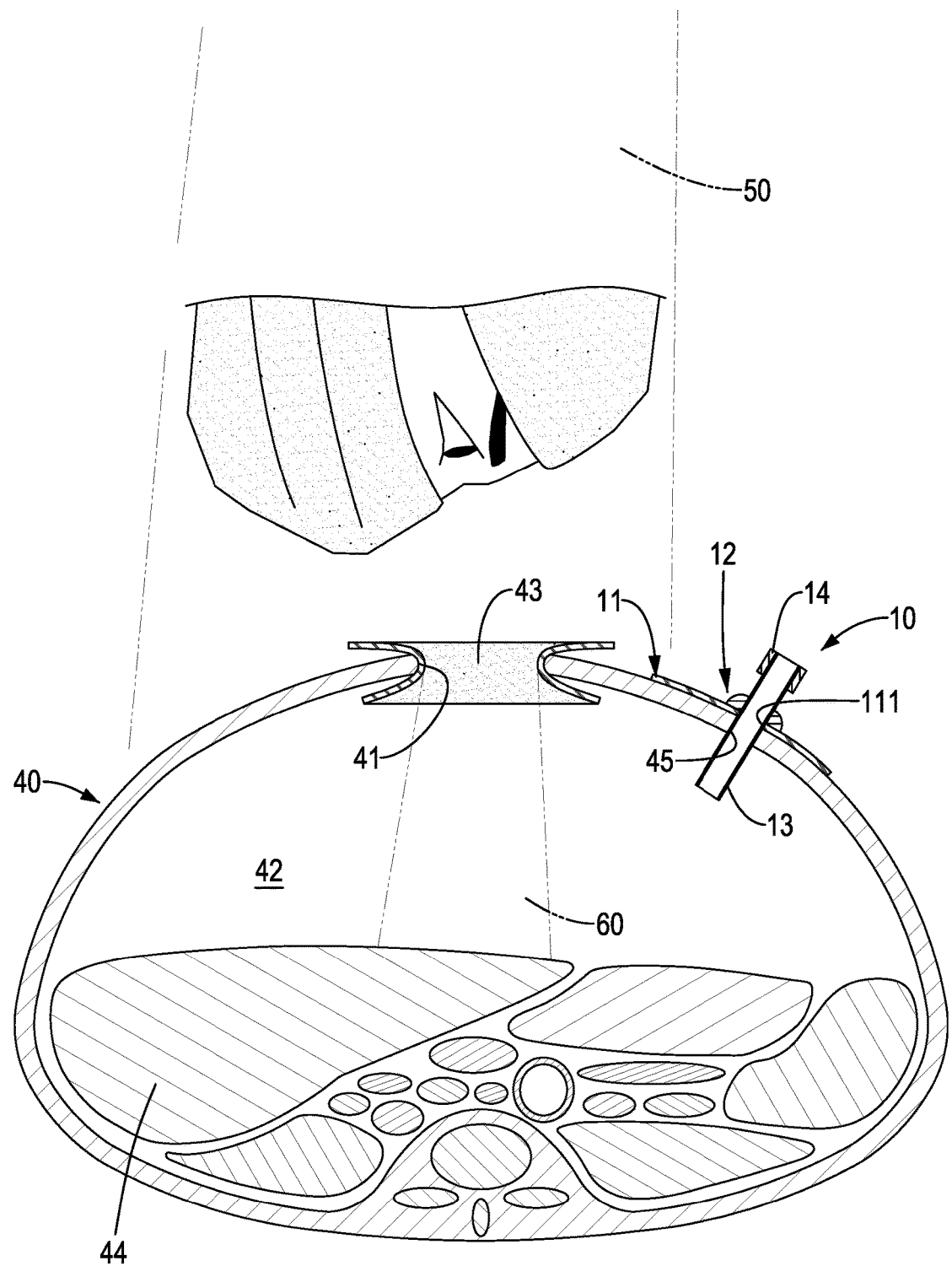
FIG. 3 is an operational side view of the body cavity illumination apparatus in FIG. 1, showing the position-controlling trocar being inserted into the peritoneal cavity of a human body.
Figure 4:
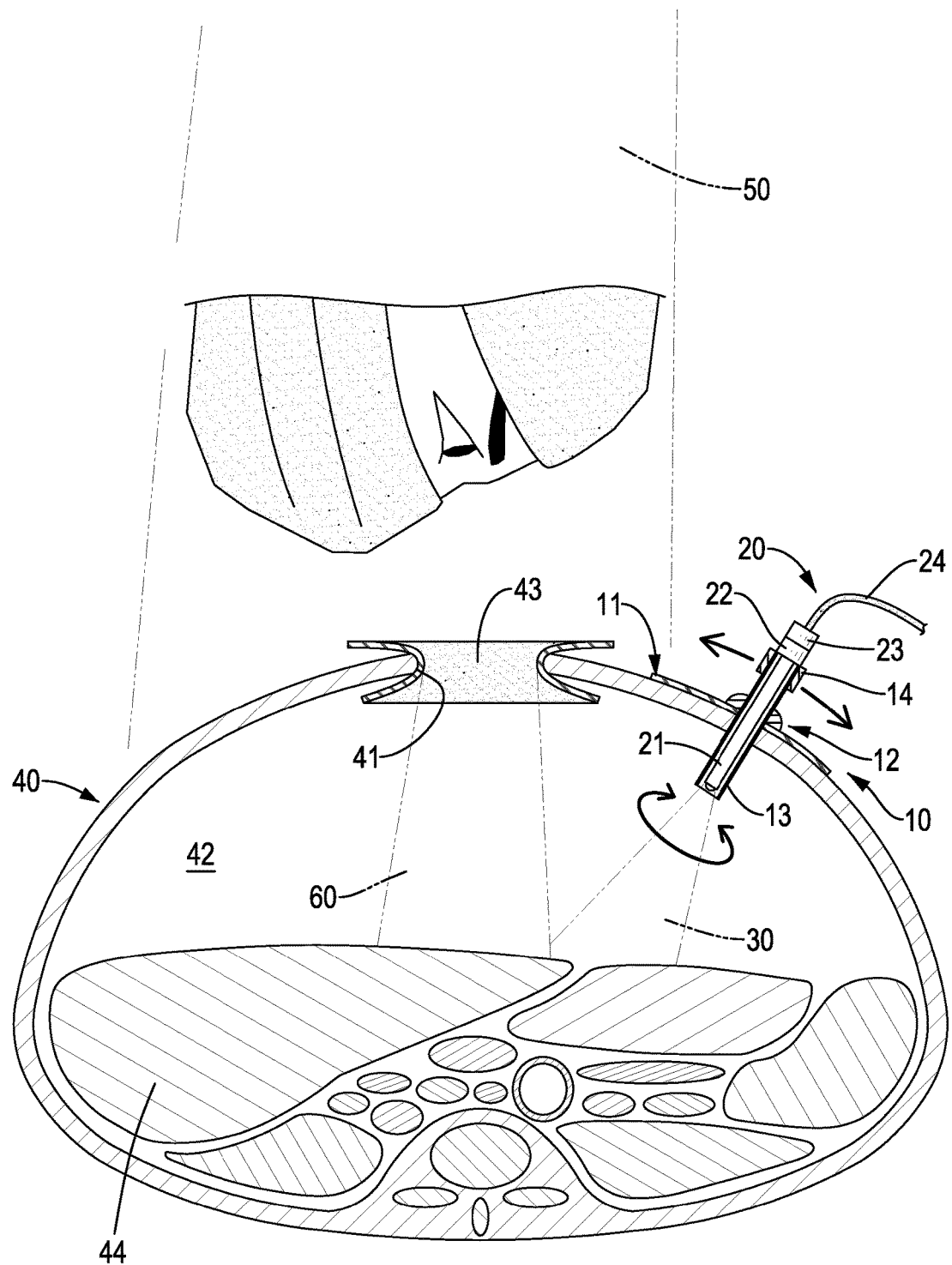
FIG. 4 is an operational side view in partial section of the body cavity illumination apparatus in FIG. 1, showing an intra-corporeal light element being inserted into the peritoneal cavity of the human body via the position-controlling trocar.

With reference to FIGS. 3 and 4, when the first embodiment of the body cavity illumination apparatus is in use, an incision 41 is formed on the human body 40 to communicate with the abdominal cavity 42 of the human body 40, and a wound retractor 43 is deposited on the abdominal wall of the human body 40 to maintain the incision 41. During surgery, an extracorporeal illumination 50 may be provided by a ceiling light, and enters the abdominal cavity 42 of the human body 40 via the incision 41 to form an interior light beam 60. Furthermore, the sticker 11 is deposited on the skin surface of the human body 40 to enable the through hole 111 to align with a surgical hole 45 of the human body 40.

After the sticker 11 is securely mounted on the skin surface of the human body 40, the trocar tube 13 extends into the abdominal cavity 42 of the human body 40 via the through hole 111 and the surgical hole 45. As the trocar tube 13 moves into the abdominal cavity 42 of the human body 40, the trocar connector 14 engages with the positioning device 12 to hold the trocar tube 13 securely on the sticker 11 relative to the human body 40. After the position-controlling trocar 10 is deposited on the human body 40, the light cable 24 of the intra-corporeal light element 20 is electrically connected to an extra-corporeal light source, and the shaft 21 is inserted into the abdominal cavity 42 of the human body 40 via the trocar connector 14, the positioning device 12, and the sticker 11, and may be contained in the trocar tube 13 to provide an intra-corporeal illumination 30 for the organs 44 of the human body 40.

Therefore, during surgery, the interior light beam 60 that is provided by the extracorporeal illumination 50 and the intra-corporeal illumination 30 that is provided by the intra-corporeal light element 20 are all emitted on the organs 44, and the surgeon may see the organs 44 of the human body 40 clearly. Additionally, when the intra-corporeal light element 20 is contained in the position-controlling trocar 10, the shaft connector 22 is connected to or engages with the trocar connector 14 to hold the intra-corporeal light element 20 to provide the intra-corporeal illumination 30 without manual holding to keep the position conveniently. Furthermore, with the structures between the sticker segment 121 and the moving segment 122 of the positioning device 12, the shaft 21 of the intra-corporeal light element 20 may rotate or swing relative to the abdominal cavity 42 of the human body 40, and this enables the intra-corporeal illumination 30 to emit light on the organs 44 at multi-angles.

Figure 5:
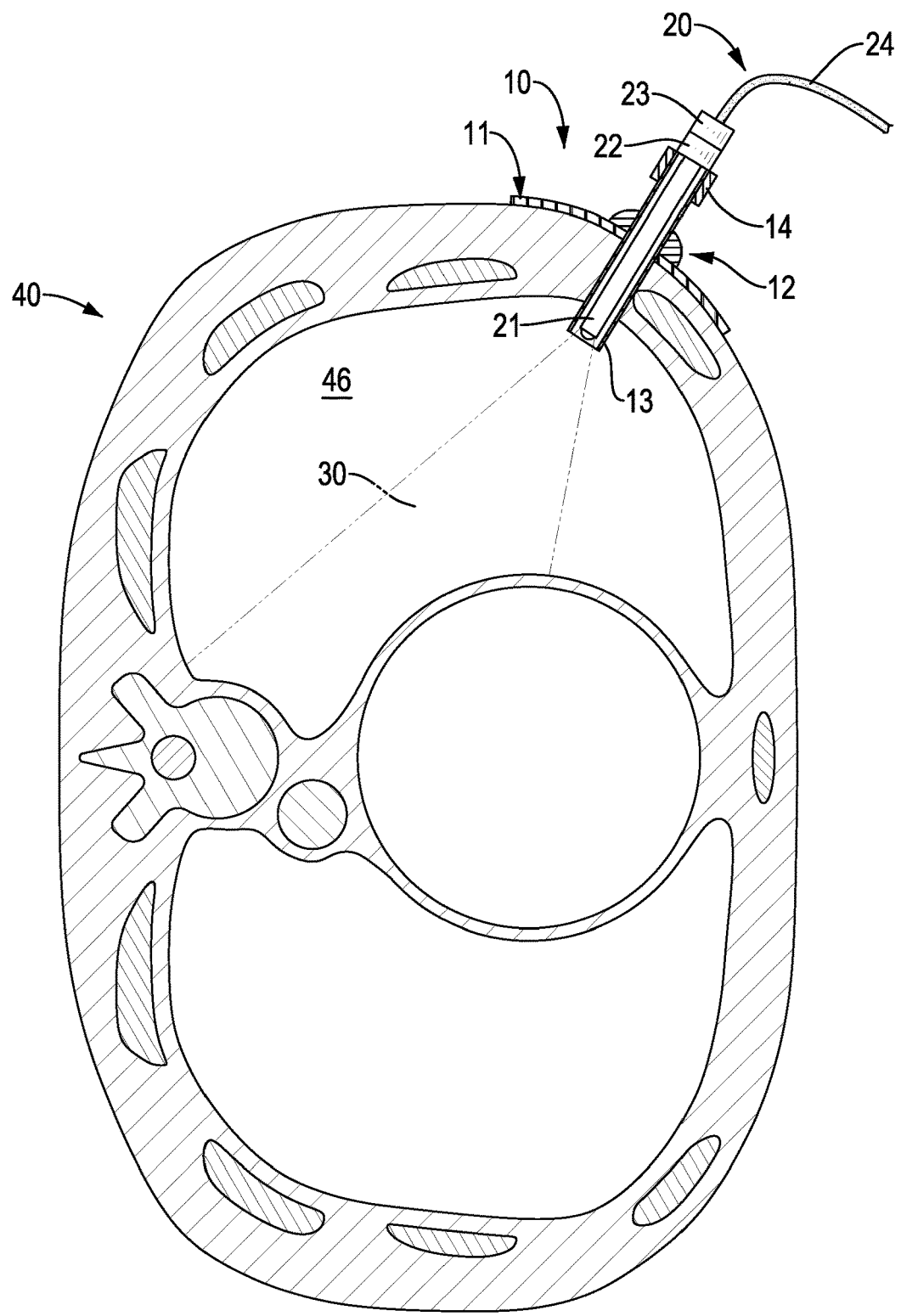
FIG. 5 is an operational side view in partial section of the body cavity illumination apparatus in FIG. 1, showing the body cavity illumination apparatus being deposited on the pleural cavity of the human body.

Furthermore, with reference to FIG. 5, the first embodiment of the body cavity illumination apparatus can be used in a pleural cavity 46 of the human body 40, and the operation of the body cavity illumination apparatus is same as the operation as described above and is not described in detail.

Figure 6:
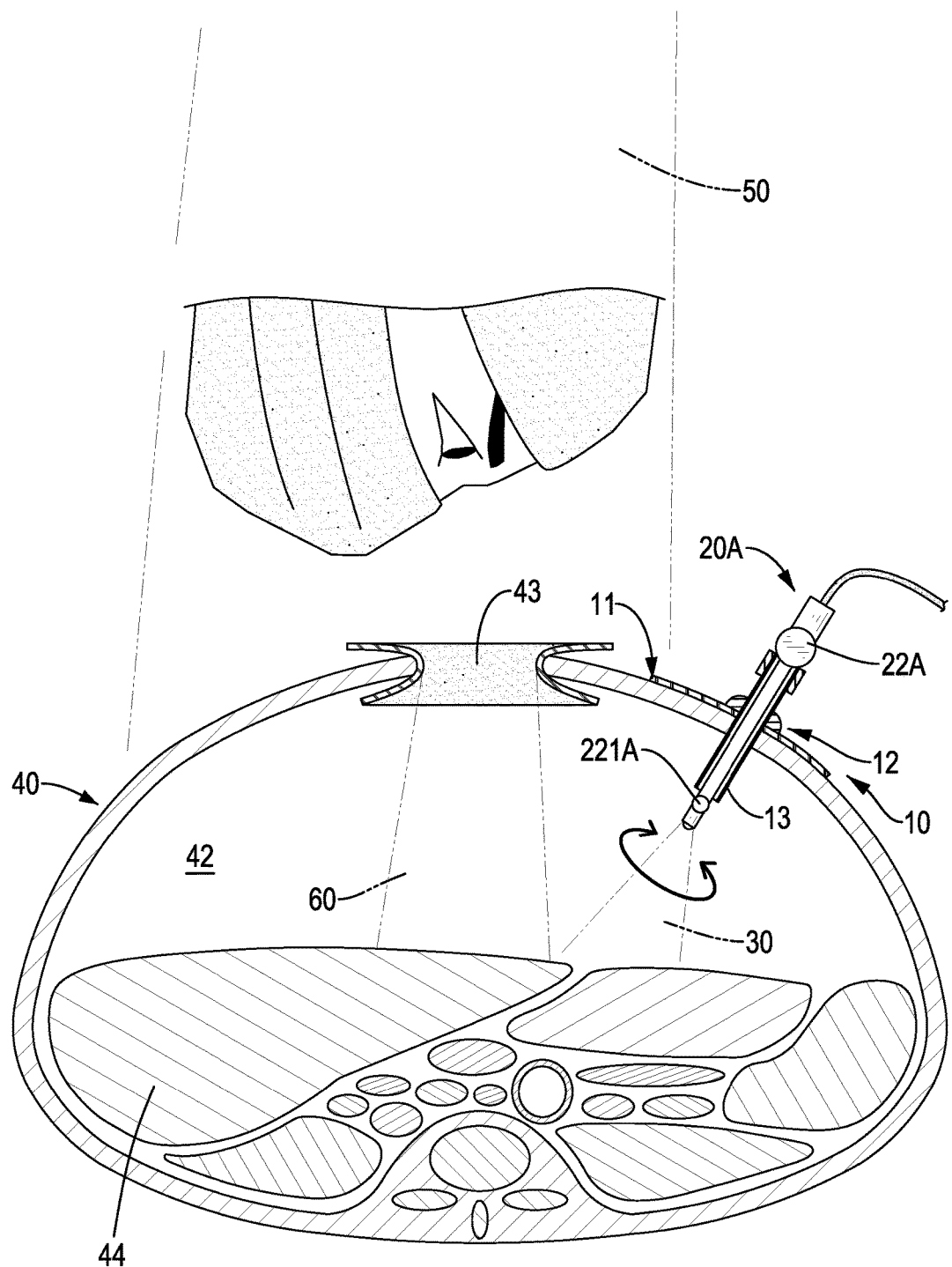
FIG. 6 is an operational side view in partial section of a second embodiment of a body cavity illumination apparatus in accordance with the present invention, showing the body cavity illumination apparatus being inserted into the peritoneal cavity of the human body.
Figure 7:
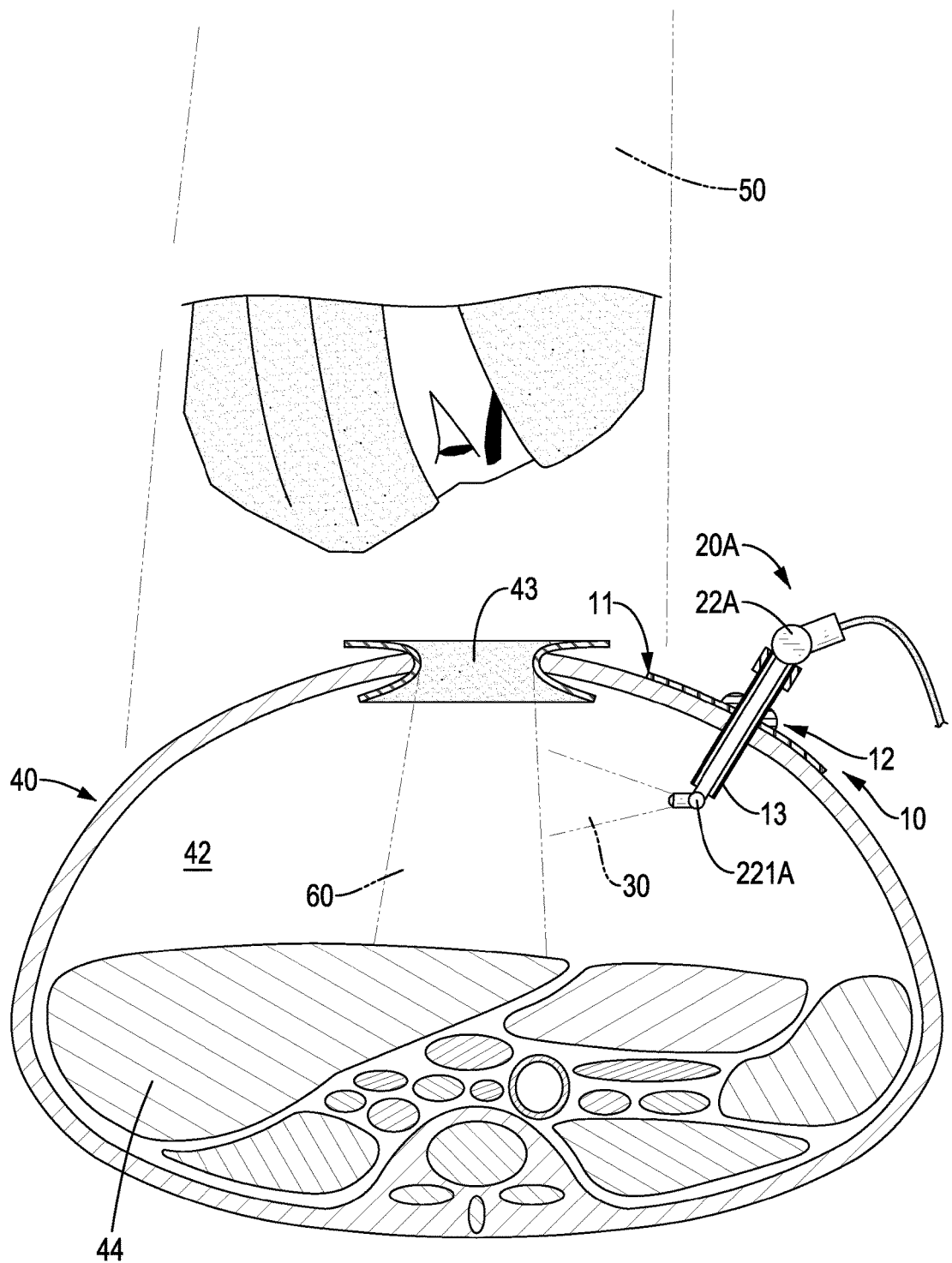
FIG. 7 is a further operational side view in partial section of the body cavity illumination apparatus in FIG. 6.

With reference to FIGS. 6 and 7, a second embodiment of a body cavity illumination apparatus in accordance with the present invention is substantially the same as the first embodiment except for the following features. The shaft connector 22A of the intra-corporeal light element 20A is a rotatable shaft connector, and has a lower rotating head 221A extending in the abdominal cavity 42 of the human body 40. The direction of the lower rotating head 221A of the shaft connector 22A can be adjusted by the shaft connector 22A. When the direction of the lower rotating head 221A of the shaft connector 22A is adjusted, the angle of the intra-corporeal illumination 30 is changed. Therefore, the surgeon may control the angle of the intra-corporeal illumination 30 by the shaft connector 22A without fighting against the resistance of the soft tissue, which tends to hold the position-controlling trocar in a position.

Figure 8:
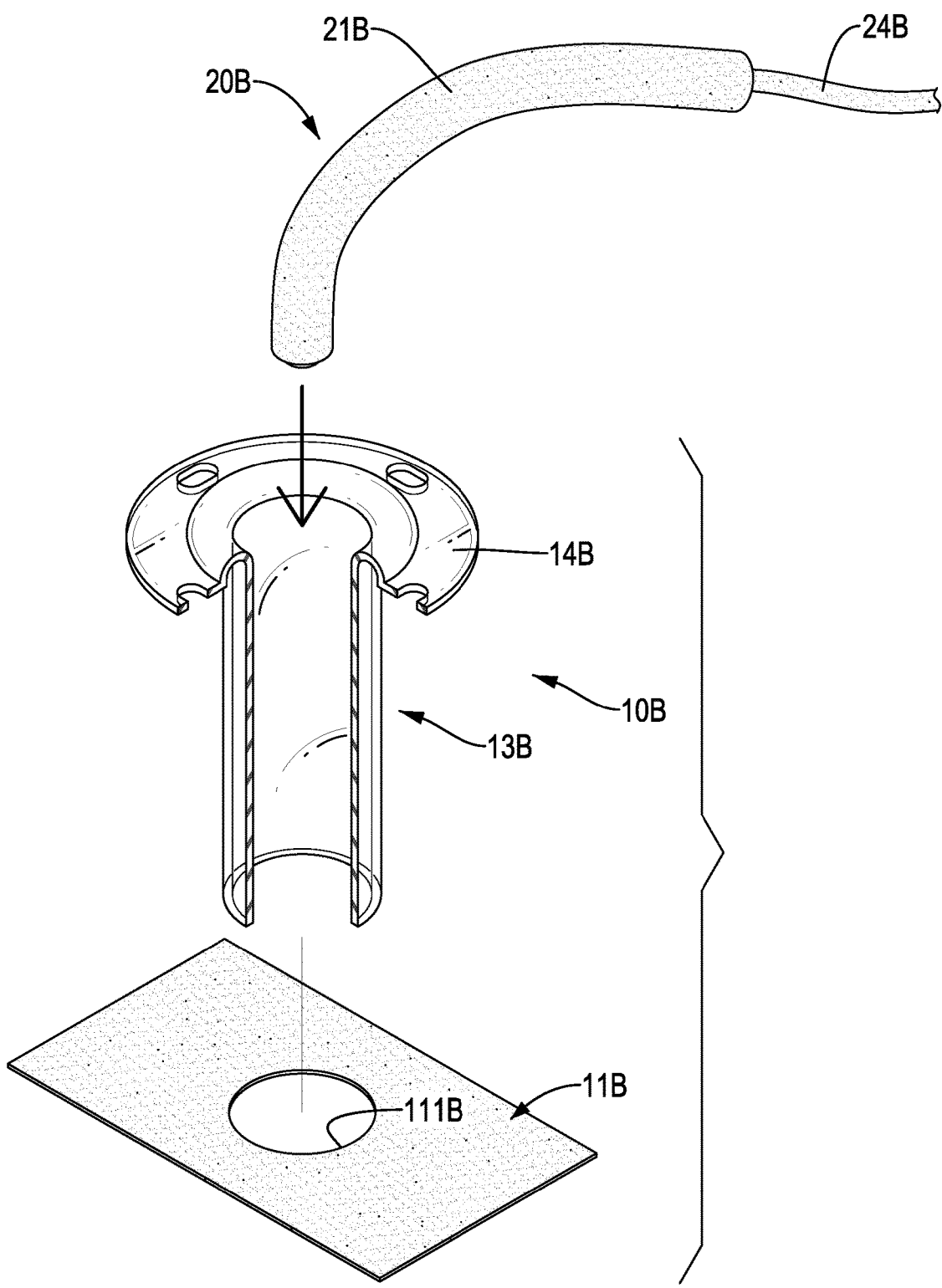
FIG. 8 is an exploded perspective view of a third embodiment of a body cavity illumination apparatus in accordance with the present invention.

With reference to FIG. 8, a third embodiment of a body cavity illumination apparatus in accordance with the present invention is substantially the same as the first embodiment except for the following features. The position-controlling trocar 10B only has the sticker 11B, the trocar tube 13B, and the trocar connector 14B without having the positioning device 12. Furthermore, the intra-corporeal light element 20B only has the shaft 21B and the light cable 24B without having the shaft connector 22 and the cable connector 23. Therefore, the total structure of the body cavity illumination apparatus can be simplified and the manufacturing cost can be reduced.

Additionally, the trocar tube 13B and the trocar connector 14B are formed with each other as a single piece, and are made of soft materials such as silicone. In addition, the trocar tube 13B may be translucent and has an inner diameter between 2 to 12 millimeters. The shaft 21B of the intra-corporeal light element 20B is curved and the light cable 24B is directly and electrically connected to the shaft 21B.

Figure 9:
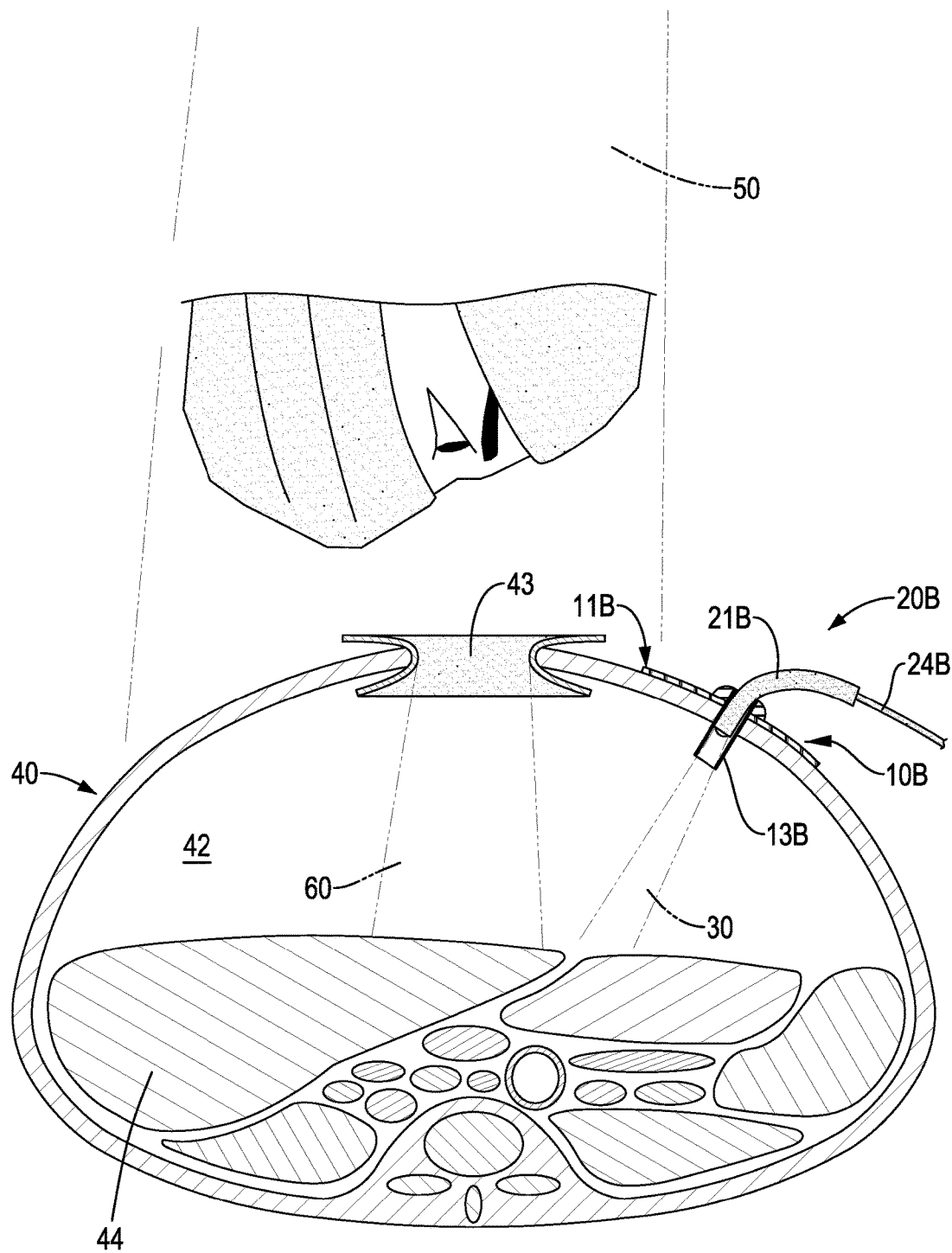
FIG. 9 is an operational side view in partial section of the body cavity illumination apparatus in FIG. 8, showing the body cavity illumination apparatus being inserted into the peritoneal cavity of the human body.
Figure 10:
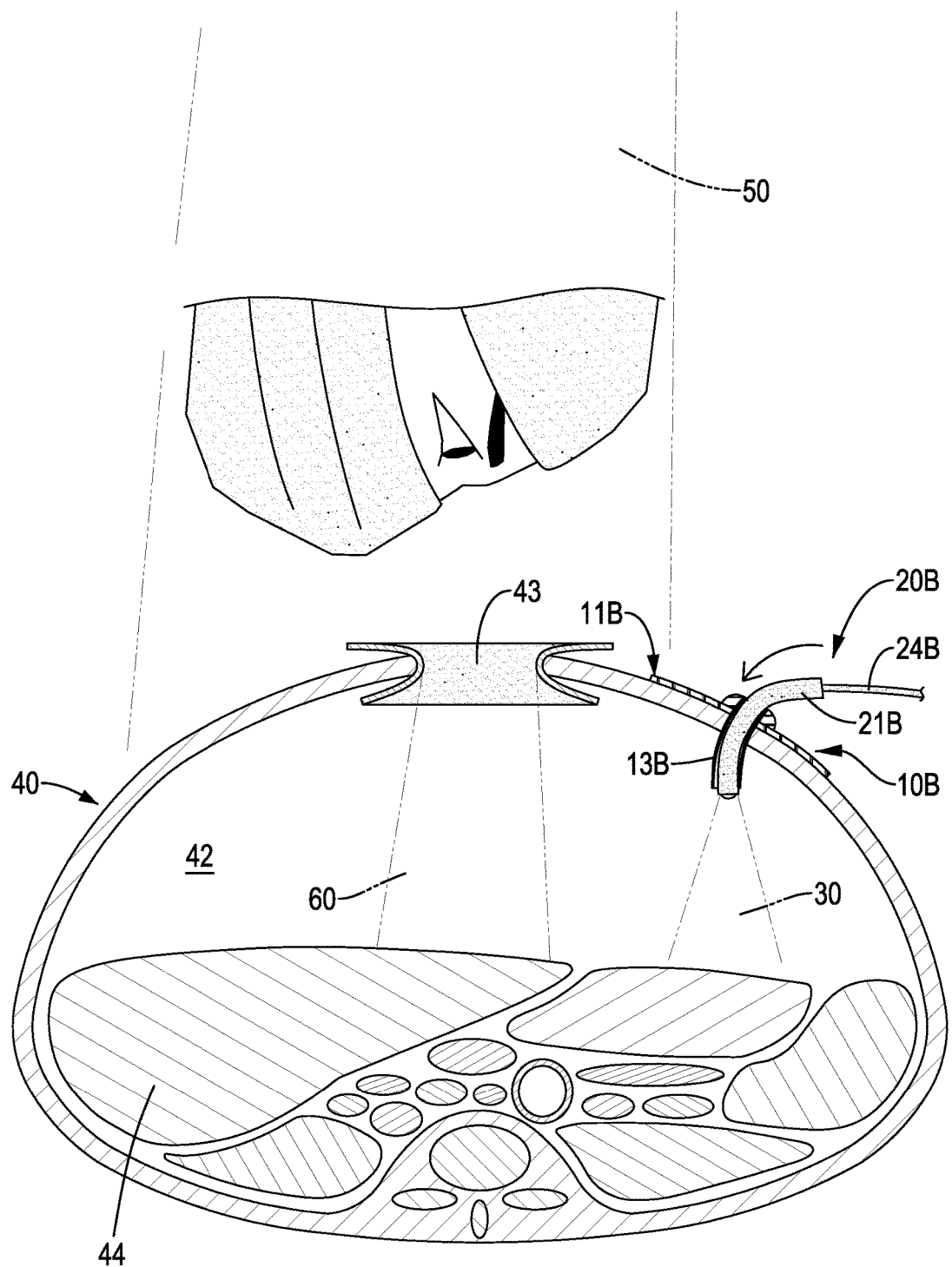
FIG. 10 is a further operational side view in partial section of the body cavity illumination apparatus in FIG. 9.
Figure 11:
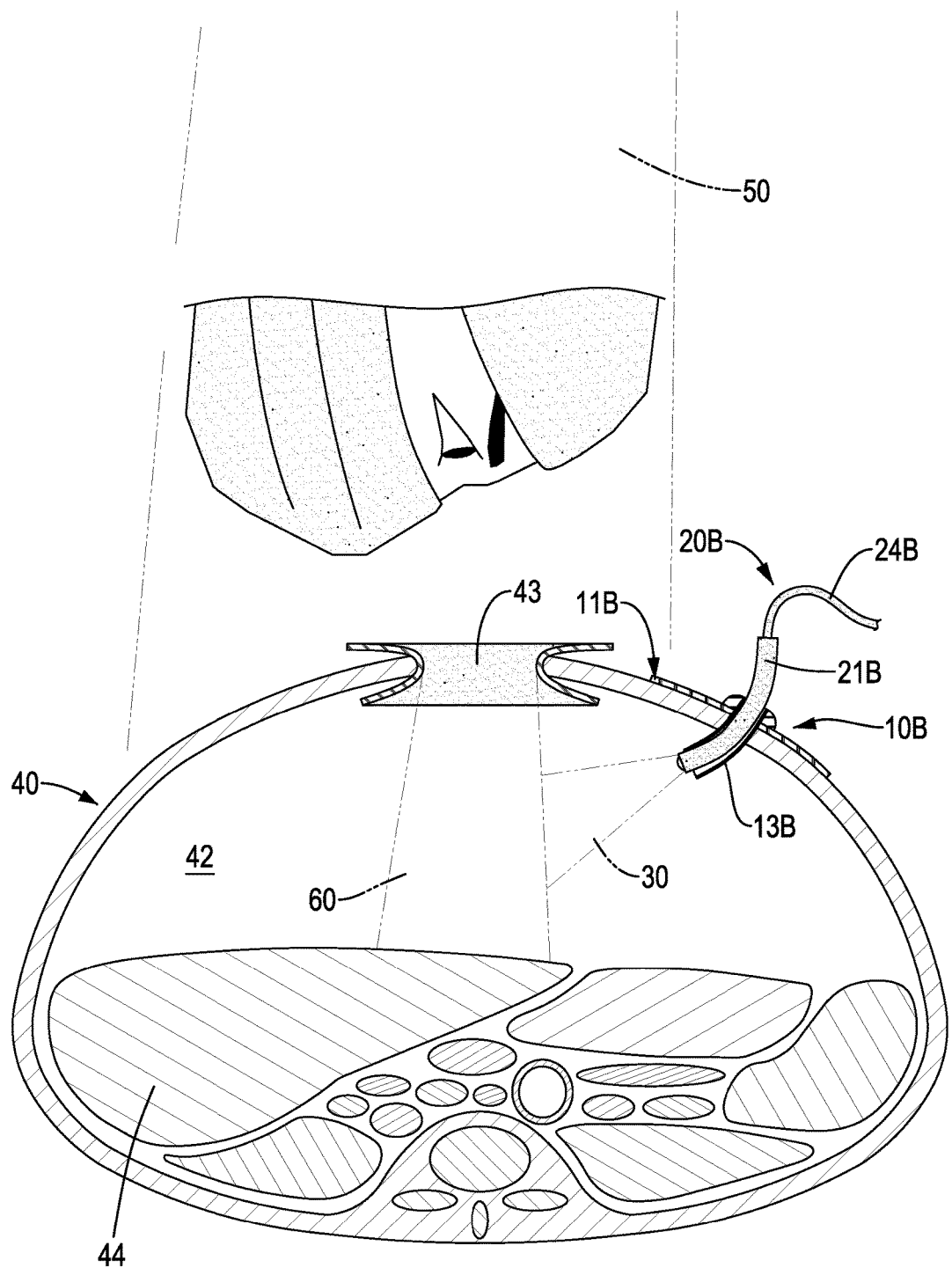
FIG. 11 is another operational side view in partial section of the body cavity illumination apparatus in FIG. 9.
Figure 12:
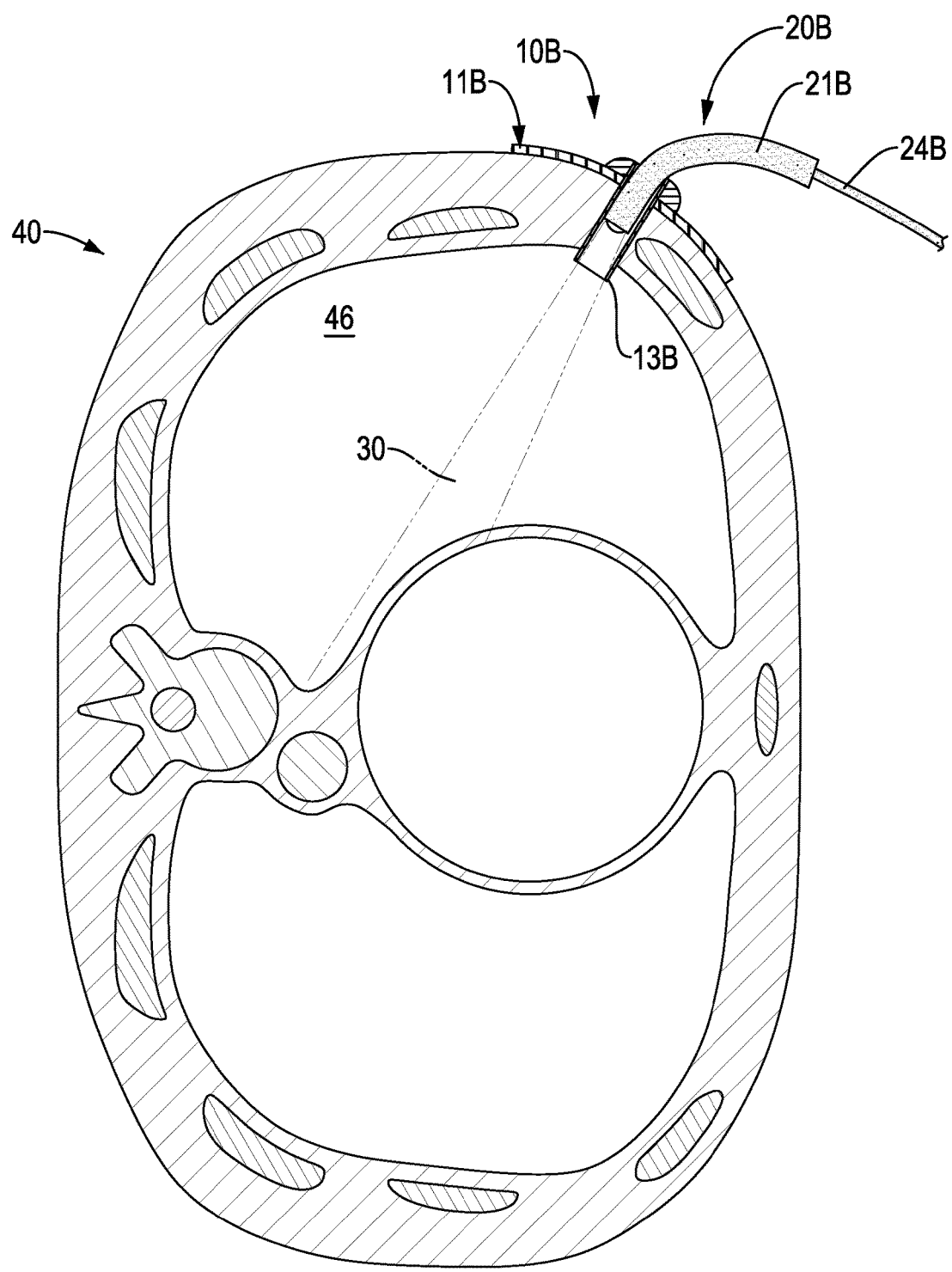
FIG. 12 is an operational side view in partial section of the body cavity illumination apparatus in FIG. 8, showing the body cavity illumination apparatus being inserted into the pleural cavity of the human body.
Figure 13:
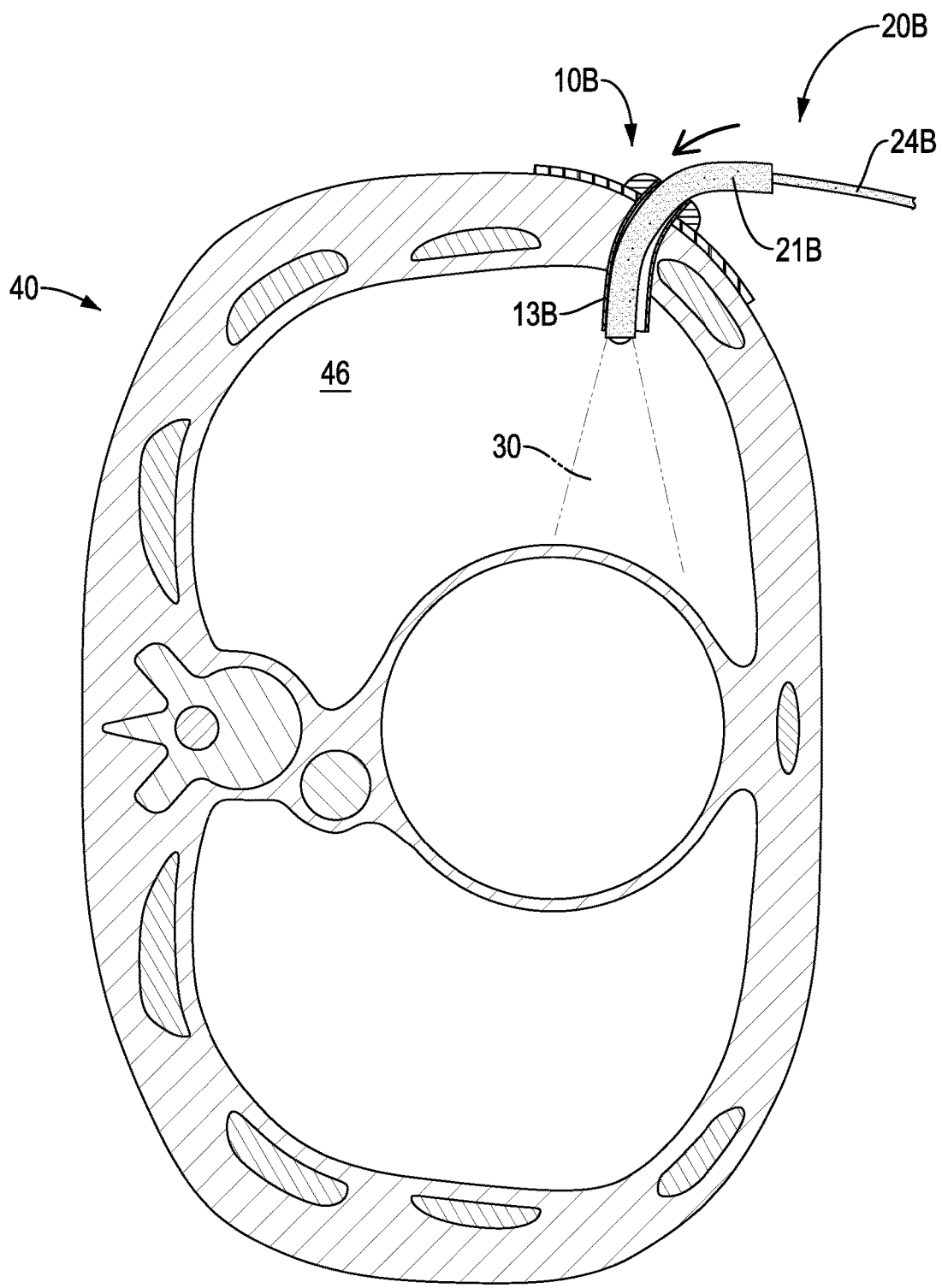
FIG. 13 is a further operational side view in partial section of the body cavity illumination apparatus in FIG. 12.
Figure 14:
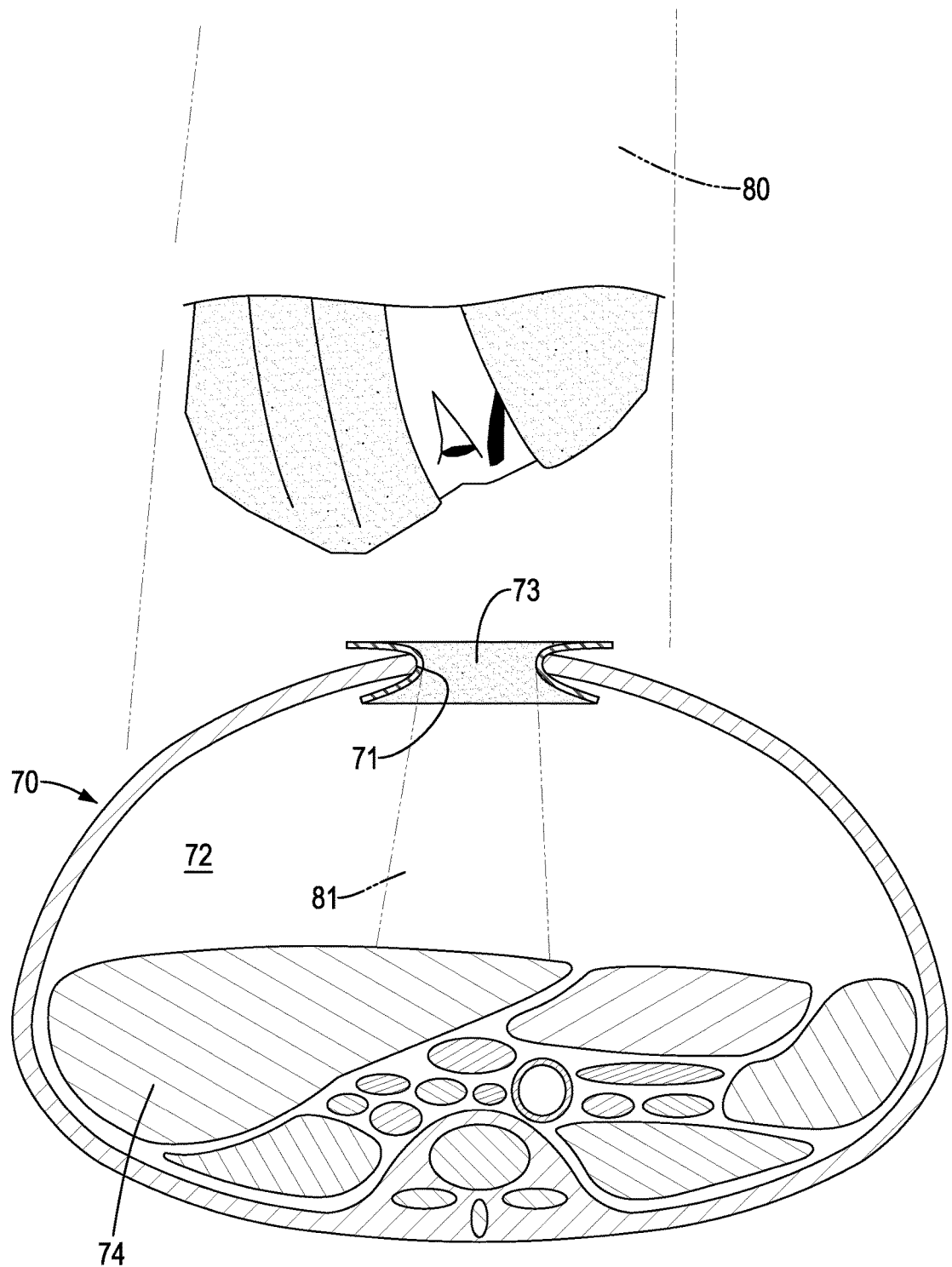
FIG. 14 is an operational side view of a body cavity illumination apparatus in accordance with the prior art.
Figure 15:
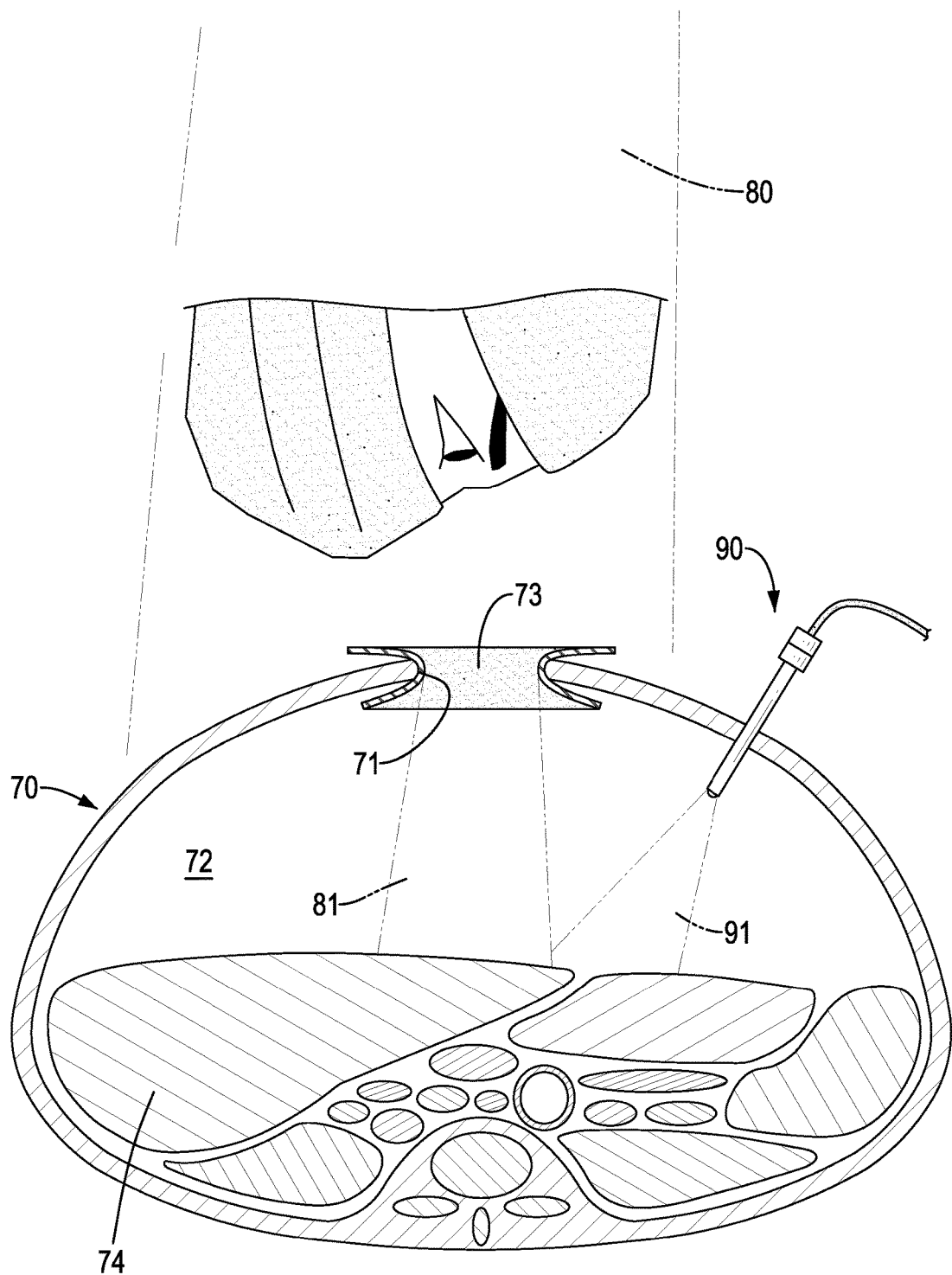
FIG. 15 is another operational side view in partial section of a body cavity illumination apparatus in accordance with the prior art.

In use, with reference to FIGS. 9, 10, and 11, the trocar tube 13B extends through the through hole of the sticker 11B and extends into the abdominal cavity 42 of the human body 40, and the trocar connector abuts the sticker 11B. The shaft 21B is inserted into the abdominal cavity 42 of the human body 40 via the trocar connector, the sticker 11B, and the trocar tube 13B. Since the shaft 21B of the intra-corporeal light element 20B is curved, the angle of the intra-corporeal illumination 30 will be changed according to the inserting depth and the rotating angle of the shaft 21B without using the structure between the sticker segment 121 and the moving segment 122 of the positioning device 12 of the first embodiment of the body cavity illumination apparatus and without fighting against the resistance of the soft tissue, which tends to hold the position-controlling trocar 10B in a position. Likewise, with reference to FIGS. 12 and 13, the third embodiment of the body cavity illumination apparatus also can be used in the pleural cavity 46 of the human body 40, and the operation of the body cavity illumination apparatus is same as the operation as described above and is not described in detail.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A body cavity illumination apparatus comprising:
   a position-controlling trocar having
      a sticker;
      a positioning device deposited on the sticker;
      a trocar tube connected to the positioning device, extending through the sticker via the positioning device, and having
         an inner end extending through the positioning device and the sticker; and
         an outer end; and
      a trocar connector connected to the outer end of the trocar tube; and
   an intra-corporeal light element detachably mounted in the position-controlling trocar, and having
      a shaft extending through the positioning device and the sticker, and extending in the trocar tube;
      a shaft connector connected to an end of the shaft that extends out of the positioning device;
      a cable connector connected to the shaft connector and being opposite the shaft; and
      a light cable connected to the cable connector and being opposite the shaft connector to connect a light source.

2. The body cavity illumination apparatus as claimed in claim 1, wherein
   the sticker has
      a bottom side;
      a top side; and
      a through hole formed through the top side and the bottom side of the sticker; and
   the positioning device has
      a sticker segment securely deposited on the top side of the sticker; and
      a moving segment detachably connected to the sticker segment of the positioning device.

3. The body cavity illumination apparatus as claimed in claim 2, wherein the moving segment is rotatably and swingably mounted on the sticker segment of the positioning device by a direct concave-convex contacting manner.

4. The body cavity illumination apparatus as claimed in claim 3, wherein the trocar connector selectively engages with the moving segment of the positioning device to hold the trocar connector and the trocar tube with the positioning device.

5. The body cavity illumination apparatus as claimed in claim 1, wherein the shaft connector of the intra-corporeal light element is a rotatable shaft connector and has a lower rotating head, and a direction of the lower rotating head of the shaft connector is adjusted by the shaft connector.

6. The body cavity illumination apparatus as claimed in claim 1, wherein the trocar connector is formed with the trocar tube as a single piece.

7. A body cavity illumination apparatus comprising:
   a position-controlling trocar having
      a sticker having
         a bottom side;
         a top side; and
         a through hole formed through the top side and the bottom side of the sticker;
      a trocar tube extending through the sticker via the through hole; and a trocar connector connected to the trocar tube and abutting the sticker; and an intra-corporeal light element detachably mounted in the position-controlling trocar, and having
a shaft being curved and extending through the sticker, and extending in the trocar tube; and
a light cable connected to the shaft.

8. The body cavity illumination apparatus as claimed in claim 7, wherein the trocar tube and the trocar connector are formed with each other as a single piece.

9. The body cavity illumination apparatus as claimed in claim 7, wherein the trocar tube and the trocar connector are made of soft materials.

10. The body cavity illumination apparatus as claimed in claim 7, wherein the trocar tube is translucent.

11. The body cavity illumination apparatus as claimed in claim 7, wherein the trocar tube has an inner diameter between 2 to 12 millimeters.

12. The body cavity illumination apparatus as claimed in claim 7, wherein an inserting depth and a rotating angle of the shaft of the intra-corporeal light element relative to a human's body is adjusted to change an angle of a light.

\* \* \* \* \*